US00PP10014P

United States Patent [19]

Meilland

[11] Patent Number: Plant 10,014

[45] Date of Patent: Sep. 2, 1997

[54] MINIATURE ROSE PLANT NAMED 'MEINIPOL'

[75] Inventor: Alain A. Meilland, Antibes, France

[73] Assignee: The Conard-Pyle Company, West Grove, Pa.

[21] Appl. No.: 708,112

[22] Filed: Sep. 4, 1996

[51] Int. Cl.[6] ..... A01H 5/00

[52] U.S. Cl. ..... Plt./9

[58] Field of Search ..... Plt./9, 7.1

[56] References Cited

U.S. PATENT DOCUMENTS

P.P. 4,480 11/1979 Moore ..... Plt./7.1

*Primary Examiner*—Howard J. Locker

*Attorney, Agent, or Firm*—Burns, Doane, Swecker & Mathis, L.L.P.

[57] ABSTRACT

A new and distinct variety of rose plant of the miniature class is provided which abundantly and substantially continuously forms attractive very double medium pink flowers which commonly are borne in clusters. The flowers tend to open slowly. The plant is erect and its dark green foliage is semi-glossy. The blossoms possess no fragrance. The plant can be grown on its own roots as attractive ornamentation in the landscape or as a decorative pot plant.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) of the new variety was the product of the pollination of the 'Lavender Jewel' variety (U.S. Plant Pat. No. 4,480) and the 'Pitica' variety U.S. Plant Pat. No. 4,017). The male parent (i.e., the pollen parent) of the new variety was the 'Meilarco' variety (U.S. Plant Pat. No. 6,170). The parentage of the new variety can be summarized as follows:

('Lavender Jewel'×'Pitica')×'Meilarco'.

The seeds resulting from the above pollination were sown and small plants were obtained which were physically and biologically different from each other. Selective study resulted in the identification of a single plant of the new variety.

It was found that the new variety of miniature rose plant of the present invention possesses the following combination of characteristics:

(a) forms in abundance in clusters attractive, very double flowers which tend to open slowly and which exhibit a medium pink coloration,
(b) exhibits an erect growth habit, and
(c) is particularly suited for growing on its own roots as an ornamental pot plant.

The new variety well meets the needs of the horticultural industry. It is particularly well-suited for use as attractive ornamentation in the landscape or for growing as a decorative pot plant.

The new variety has been found to undergo asexual propagation in France by a number of routes, including budding, grafting, and cuttage. Asexual propagation by the above-mentioned methods as performed in France has shown that the characteristics of the new variety are strictly transmissible from one generation to another.

The new variety has been named the 'Meinipol' variety.

BRIEF DESCRIPTION OF THE PHOTOGRAPH

The accompanying photograph shows as nearly true as it is reasonably possible to make the same, in a color illustration of this characters, typical specimens of the plant parts of the new variety. The rose plants of the new variety were one year of age and were observed during September while growing on their own roots indoors at Le Cannet des Maures, Var, France. Dimensions in centimeters are shown at the bottom of the photograph.

FIG. 1—illustrates a specimen of a young shoot;

FIG. 2—illustrates specimens of two floral buds before the opening of the sepals;

FIG. 3—illustrates specimens of two floral buds at the opening of the sepals;

FIG. 4—illustrates specimens of two floral buds at the opening of the petals;

FIG. 5—illustrates specimens of two flowers during the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets with the upper surface being shown at the right and the under surface being shown at the left; and FIG. 15—illustrates specimens of leaves with five leaflets with the upper surface being shown at the bottom and the under surface being shown at the top.

DETAILED DESCRIPTION

Figures 1, 2, 3, 4, 5, 6, 7, 8, 9, 10, 11, 12, 13, 14, 15:
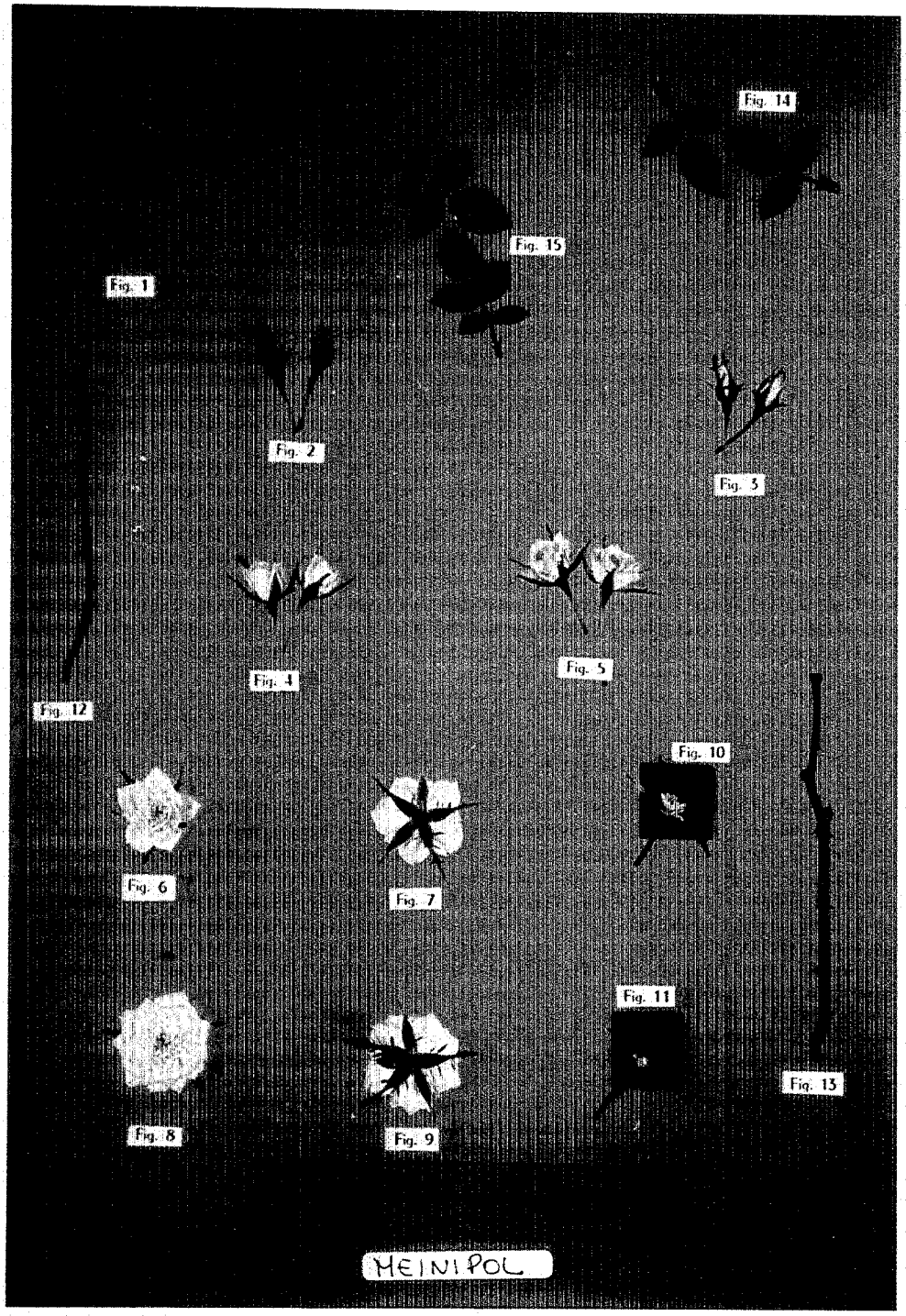

The chart used in the identification of the colors is that of The Royal Horticultural Society (R.H.S. Colour Chart). The terminology which precedes reference to the chart has been added to indicate the corresponding colors in more common terms. The description is based on one year-old specimens of the new variety which were observed during October while growing on their own roots indoors at Le Cannet des maures, Var, France.

Class: Miniature.

Plant:

*Height.*—Approximately 30 cm. on average at the end of the growing season.

*Habit.*—Erect.

Branches:

*Color.*—Young stems: Lettuce Green, Yellow-Green Group 144B. Adult wood: light green, Green Group 137C.

*Thorns.*—Size: small. Quantity: numerous. Color: greenish.

Leaves:

*Petioles.*—Upper surface: striped, reddish on young foliage and medium green on mature foliage with few glandular edges. Under surface: light green and bear some small thorns.

*Stipules.*—adnate, pectinate, rather narrow and linear.

*Leaflets.*—Number: 3, 5 (most often), and 7.Shape: lanceolate. Texture: consistent. General appearance: dense, dark green, and semi-glossy foliage. Color (young foliage): Upper surface: Lettuce Green, Yellow-Green Group 144A, and edged with reddish-brown coloration. Under surface: Lettuce Green, Yellow-Green Group 144C, and suffused with reddish-brown coloration. Color (adult foliage): Upper surface: dark green, Green Group 137A. Under surface: Greyed-Green Group 191A.

Inflorescence:

*Number of flowers.*—Multiflorous, and commonly with approximately 2 to 5 flowers per stem.

*Peduncle.*—Medium green in coloration, smooth, and the length is approximately 5.5 cm. on average.

*Sepals.*—Upper surface: tomentose and greenish in coloration. Under surface: medium green with a few extensions.

*Buds.*—Shape: conical. Length: approximately 1.5 cm. on average. Size: medium. Color upon opening: Upper surface: Red Group 52B at the margins, and Red Group 56B towards the middle. Under surface: Red Group 52B at the margins, and Red Group 56B towards the middle.

*Flower.*—Form: cupped with a deep center. Diameter: approximately 4 cm. on average. Color (when opening begins): Upper surface: at the margins near Red Group 56B and widely suffused with Red Group 55A, and at the middle near Red Group 56B with a light yellowish cast. Under surface: near Red Group 56B and suffused with Red Group 55A. Color (when blooming): Upper surface: the external petals at the margins are near Red Group 56B and suffused with Red Group 55B, and at the middle are Red Group 56B and lightly suffused with Red Group 55B, and the coloration of the internal petals tends to be stronger and more pronounced than that of the external petals. Under surface: near Red Group 56D, and edged with Red Group 55B with some whitening on the external petals. Color (at end of blooming): Upper surface: near Red Group 49D and lightly suffused with Red Group 55B. Under surface: near Red Group 49D and lightly suffused with Red Group 55B, commonly with some whitening on external petals. Fragrance: none. Petal number: approximately 75 on average. Petal shape: the base is obtuse and the tip is lanceolate with reflexed edges. Petal drop: good with the petals commonly detaching cleanly. Anthers: normal and ochre in coloration. Stamen number: approximately 70 on average. Filaments: normal and yellowish in coloration. Pistil number: approximately 40 on average. Stigmas: greenish in coloration. Styles: pinkish in coloration. Receptacle: medium green, smooth, and in longitudinal section in the shape of a pitcher.

Development:

*Vegetation.*—Strong.

*Blooming.*—Abundant and substantially continuous.

*Resistance to diseases.*—Good.

I claim:

1. A new and distinct variety of miniature rose plant characterized by the following combination of characteristics:

(a) forms in abundance in clusters attractive very double flowers which tend to open slowly and which exhibit a medium pink coloration,
(b) exhibits an erect growth habit, and
(c) is particularly suited for growing on its own roots as an ornamental pot plant;

substantially as herein shown and described.

* * * * *

HEINIPOL